United States Patent [19]

Jouquey et al.

[11] Patent Number: 4,529,713
[45] Date of Patent: Jul. 16, 1985

[54] RADIOACTIVE STILBENE DERIVATIVES IN RADIOIMMUNOASSAY

[75] Inventors: Alain Jouquey; Gaëtan Touyer, both of Paris, France

[73] Assignee: Roussel Uclaf, Paris, France

[21] Appl. No.: 390,938

[22] Filed: Jun. 22, 1982

[30] Foreign Application Priority Data

Jul. 1, 1981 [FR] France .................. 81 12934

[51] Int. Cl.³ .......................... G01N 33/56
[52] U.S. Cl. ..................... 436/545; 436/804; 548/337; 560/40; 560/61; 562/444; 562/471; 564/174
[58] Field of Search ........... 548/337; 564/174; 23/230.3; 560/40; 562/444; 436/545, 804

[56] References Cited
U.S. PATENT DOCUMENTS 4,310,675 1/1982 Akerkar et al. .................. 548/337 X

OTHER PUBLICATIONS

Gutierrez-Cernosek, R., et al., *Ann. Clin. Lab. Sci.* 7(1), 35(1977).
Fruton, J., et al., *General Biochemistry*, John Wiley, New York, 1953, p. 672.
Raith, L., *Introduction to Radioimmunoassay Methods*, Kirn and Birner, Frankfurt, 1975, pp. 3-31.
*Chemical Abstracts*, Chemical Subject Index to 9th Collective Edition, p. 27736cs, (1976).
*Chemical Abstracts*, 92:41489j, (1980) [Johnson, et al., *J. Labelled Compd. Radiopharm.*, 1979, 16(3), 501-6].
Hunter, W., in *Handbook of Exp. Immunology*, 2nd ed., 1973, pp. 17.1-17.35.

*Primary Examiner*—Richard A. Schwartz
*Attorney, Agent, or Firm*—Charles A. Muserlian

[57] ABSTRACT

Novel radioactive stilbene derivatives marked with iodine 125 or 131 of the formula

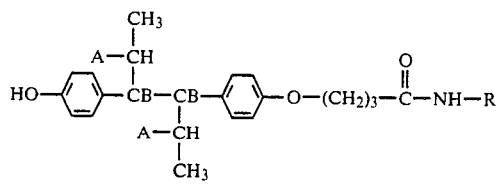

wherein each A and B are both hydrogen or together form a double bond and R is the remainder of amino acid of the formula R—NH₂ or a derivative thereof possessing an iodine acceptor group and marked with iodine 125 or 131 and their preparation and antigens obtained therefrom and a process for preparing said antigens.

5 Claims, No Drawings

RADIOACTIVE STILBENE DERIVATIVES IN RADIOIMMUNOASSAY

STATE OF THE ART

Radioimmunological dosages of stilbenes and especially of diethylstilbestrol are described in "Compte-Rendu Academie des Sciences de Paris t. 277, 5 Nov. 1973 Série D p. 1921–1924", in "Rec. Med. Vet. 1978 154 (5) 441–450" and in "The Veterinary Quaterly Vol. 3 No. 4 Oct. 1981". Dosages of hexoestrol residues are described in "J. Vet. Pharmacol. Therap. 3, 245–254 (1980). In these radioimmunological dosages, compounds marked with Tritium are used.

Also pertinent is "J. of Labelled Compounds and Radiopharmaceutical Vol. XVI No. 3 p. 501–506 (1979)". In this document, an amide formed with histamine and diethylstilbestrol 4-O-(carboxypropyl) substituted on the histamine residue with iodine 125 is described by H. J. Johnson, S. F. Cernosek and R. M. Gutierrez-Cernosek. But this compound is badly defined. Moreover, it permits only the radioimmunological dosage of diethylstilbestrol and that, with slight precision. In short, it does not permit the dosage of other stilbenes such as dienestrol and hexestrol. On the other hand, the compounds of formula I of the present invention permit not only the dosage with great precision of dienestrol and hexestrol but also of diethylstilbestrol. In support of that the possible analysis of traces of these stilbenes in carcasses, tissues, corporeal liquids, excretions of bovines can be cited as examples.

OBJECTS OF THE INVENTION

It is an object of the invention to provide the novel stilbene derivatives of formula I and a novel process for their preparation and novel intermediates.

It is another object of the invention to provide a novel method of using the compounds of formula I for radioimmunological dosages in tissues of warm-blooded animals and in aliments therefore.

It is a further object of the invention to provide novel antigens derived from the compounds of formula I and a method for preparing the said antigens.

It is an addition object of the invention to use the antigens to prepare antibodies.

These and other objects and advantages of the invention will become obvious from the following detailed description.

THE INVENTION

The novel compounds of the formula are radioactive stilbene derivatives marked with iodine 125 or 131 of the formula

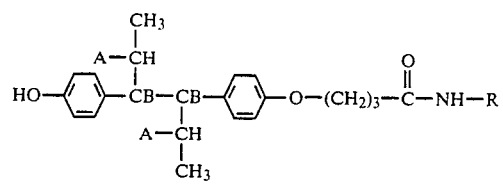

wherein each A and B are both hydrogen or together form a double bond and R is the remainder of amino acid of the formula $R-NH_2$ or a derivative thereof possessing an iodine acceptor group and marked with iodine 125 or 131.

Examples of derivatives of amino acids are the decarboxyl derivative of an amino acid or a lower alkyl ester of an amino acid. Especially preferred are the amino acid groups selected from the group consisting of histidine, tyrosine, histamine, tyramine and methyl tyrosinate marked with 125 or 131 iodine.

Among the preferred compounds of formula I are 4-O-monocarboxypropyl-dienestrol coupled with ($^{125}$I) histamine of the formula

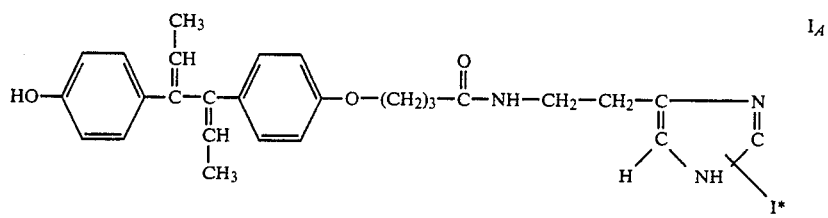

where I* is radioactive $^{125}$I in the 2- or 5-position and 4-O-monocarboxypropyl-hexestrol coupled with ($^{125}$I) histamine of the formula

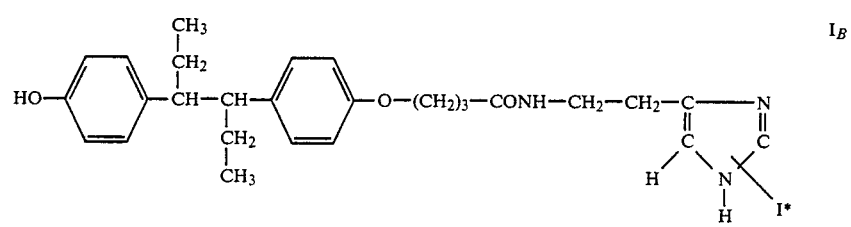

where I* is radioactive $^{125}$I in the 2- or 5-position.

The novel process of the invention for the preparation of the compounds of formula I comprises reacting a compound of the formula

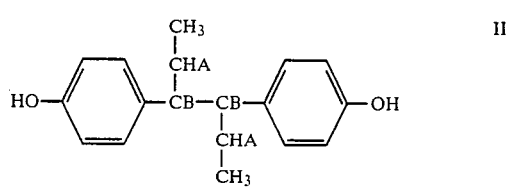

wherein A and B have the above definition with an alkyl halobutyrate in the presence of a base to obtain an ether of the formula

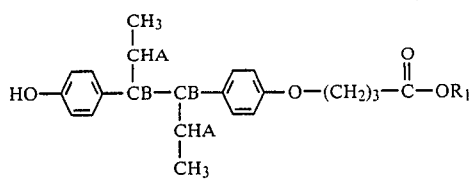

wherein $R_1$ is alkyl of 1 to 6 carbon atoms, saponifying the latter to obtain a compound of the formula

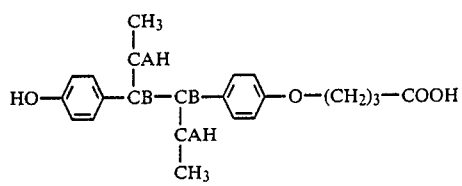

reacting the latter compound to fix on the carboxyl group an activating group for the carbonyl function to obtain a compound of the formula

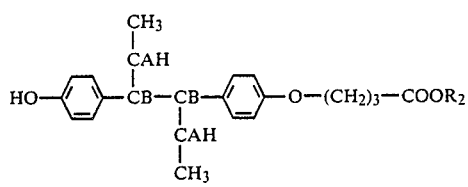

wherein $R_2$ is an activating group for the carbonyl function of the formula

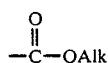

and Alk is alkyl of 1 to 6 carbon atoms and reacting the latter with an amino acid possessing an iodine acceptor group or a derivative of the said acid to obtain a compound of formula I.

The amino acid or derivative thereof possessing an iodine acceptor group may be histidine, tyrosine, histamine, tyramine and methyl tyrosinate and the compound of formula IV may be reacted under anhydrous conditions with a lower alkyl haloformate in the presence of a tertiary base under an inert atmosphere to obtain the compound of formula V.

In a preferred mode of the said process, the compound of formula II is reacted with ethyl bromobutyrate in the presence of potassium carbonate and the alkyl ester group is saponified with sodium methanolate. The compound of formula IV is preferably reacted with isobutyl chloroformate in the presence of tri-n-butylamine in anhydrous dioxane and under an inert atmosphere and the compound of formula V is preferably reacted with histamine marked with $^{125}I$ or $^{131}I$ under an inert atmosphere. The activation of the carbonyl group of the compound of formula IV may be effected by reaction with N-hydroxy-succinimide or dicyclohexylcarbodiimide to generate activating groups for the carbonyl function.

The process of the invention is especially useful for the preparation of the compound of formula $I_A$ starting from dienestrol or the compound of formula $I_B$ starting from hexestrol.

The compounds of formula I are useful for radioimmunological dosages of dienestrol and hexestrol as well as diethylstilbestrol in bile, urine, feces, plasma and animal and human tissues and in ailments of humans and warm-blooded animals.

The novel intermediates of the invention for the preparation of the compounds of formula I are the compounds of formulae III, IV and V, which can be represented by the formula

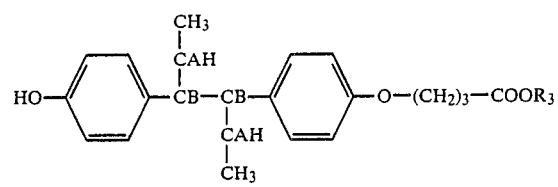

wherein $R_3$ is selected from the group consisting of hydrogen, alkyl of 1 to 6 carbon atoms and a carbonyl activating group and each A and B are hydrogen or form a double bond.

The preferred intermediate products of the invention are 4-O-monocarbethoxypropyl-dienestrol of the formula

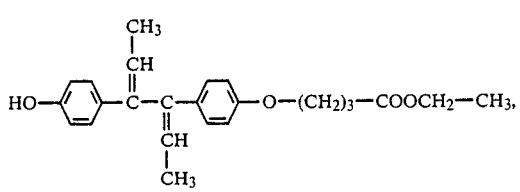

4-O-monocarbethoxypropyl-hexestrol of the formula

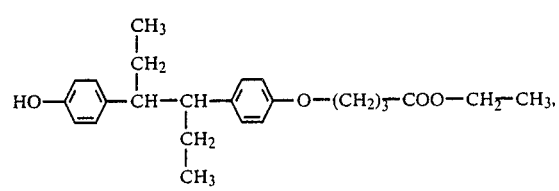

4-O-monocarboxypropyl-dienestrol of the formula

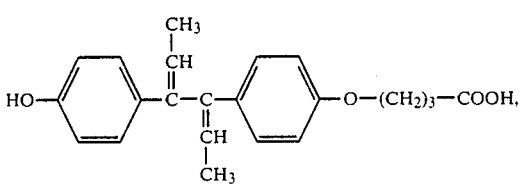

4-O-monocarboxypropyl-hexestrol of the formula

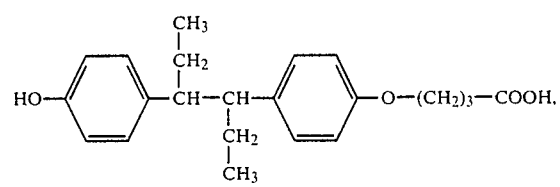

the mixed anhydride of 4-O-monocarboxypropyl-dienestrol and isobutyl formate of the formula

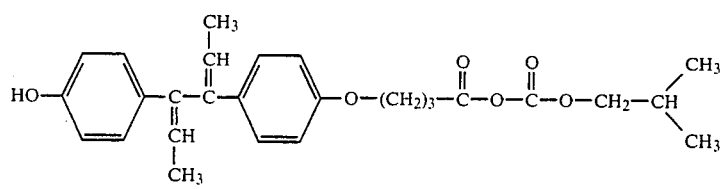

and the mixed anhydride of 4-O-monocarboxypropyl-hexestrol and isobutyl formate of the formula

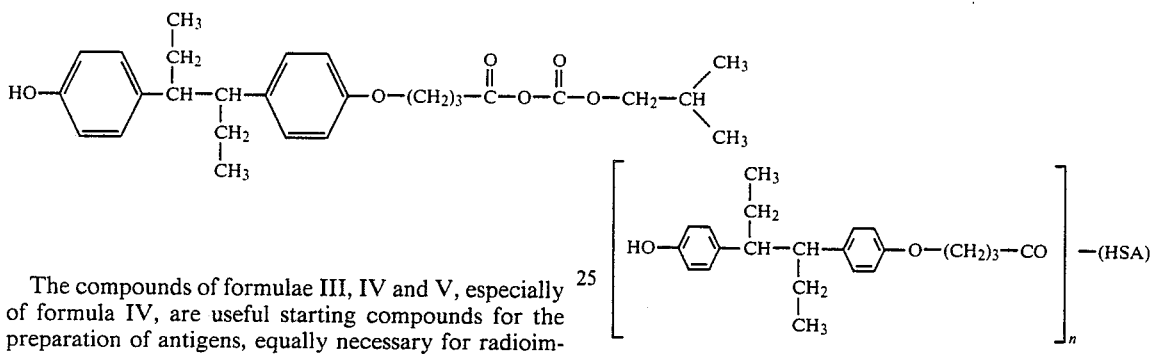

The compounds of formulae III, IV and V, especially of formula IV, are useful starting compounds for the preparation of antigens, equally necessary for radioimmunological dosages of diethylstilbestrol, dienestrol or hexestrol characterized by conjugation with bovine seric albumin (BSA) or human seric albumin (HSA) to obtain an antigen.

Examples of preferred antigens are antigens starting from 4-O-monocarboxylpropyl-dienestrol of the formula

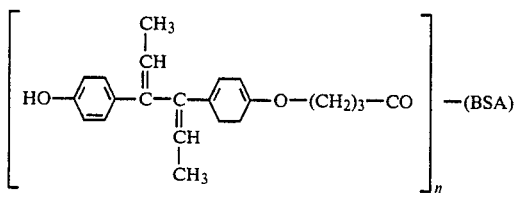

wherein n is 20 to 40 and

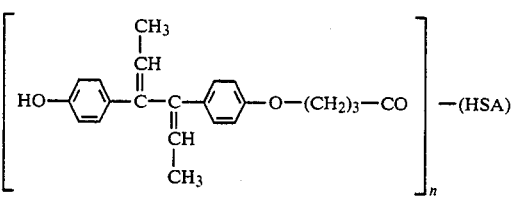

wherein n is 20 to 40 and antigens starting from 4-O-monocarboxypropyl-hexestrol of the formula

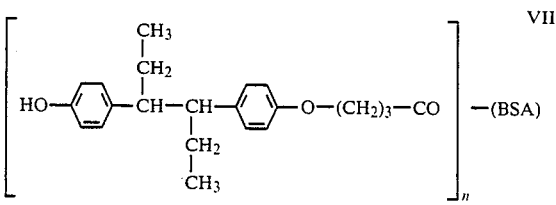

wherein n is 20 to 40 and

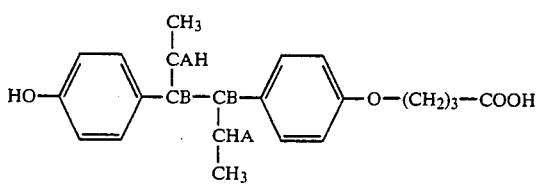

wherein n is 20 to 40.

The preferred process of the invention for the preparation of antigens of the invention comprises reacting a compound of formula IV

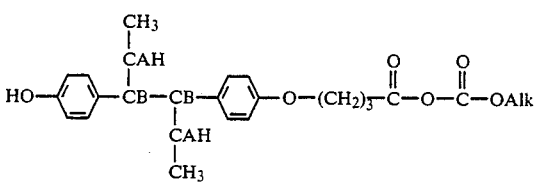

with an alkyl haloformate in the presence of a tertiary base under anhydrous conditions and an inert atmosphere to form a mixed anhydride of the formula $$\text{HO}-\bigcirc-\underset{\underset{\underset{CH_3}{|}}{\overset{\overset{CH_3}{|}}{CAH}}}{CB}-\underset{\underset{\underset{CH_3}{|}}{\overset{\overset{CAH}{|}}{CB}}}{}-\bigcirc-O-(CH_2)_3-\overset{O}{\overset{\|}{C}}-O-\overset{O}{\overset{\|}{C}}-OAlk$$

wherein Alk is alkyl of 1 to 6 carbon atoms and conjugating the latter with bovine seric albumin (BSA) or human seric albumin (HSA) to obtain the desired antigen.

In the preferred mode of the latter process, the compound of formula IV is reacted with isobutyl chloroformate in anhydrous dioxane in the presence of tri-n-butylamine at 4° C. under an inert atmosphere and the mixed anhydride is reacted with a solution of bovine seric albumin or human seric albumin in a mixture of water and dioxane under an inert atmosphere.

The novel method of the invention for the preparation of antibodies comprises administering to warm-blooded animals an antigen of the invention in the presence of an adjuvant to obtain serum containing antibodies against hexestrol or dienestrol and against diethylstilbestrol.

The compounds of formula I and especially 4-O-monocarboxypropyl-dienestrol ($^{125}$I) histamine and 4-O-monocarboxypropyl-hexestrol ($^{125}$I) histamine are used in radioimmunological dosage of dienestrol, hexestrol and diethylstilbestrol and permits dosage of stilbenes in biological liquids and tissues and in human and animal alimentation. The radioimmunological dosage is effected by the method of Bergson et al [Hormone, Vol. 4 (1964), p. 557] and Abraham [Journal of Chemical Endocrinonal metab, Vol. 29 (1969), p. 866].

In the following examples there are described several preferred embodiments to illustrate the invention. However, it should be understood that the invention is not intended to be limited to the specific embodiments.

EXAMPLE 1

4-O-monocarboxypropyl-dienestrol coupled with ($^{125}$I) histamine

STEP A: 4-O-monoethoxycarbonylpropyl-dienestrol

A mixture of 20 g of dienestrol, 7 g of ethyl bromobutyrate and 4.6 g of dry potassium carbonate in 300 ml of acetone was refluxed for 17 hours and was then cooled to room temperature and was poured into water. The mixture was extracted with ethyl acetate and the organic phase was washed with water, dried, treated with activated carbon and filtered. The filtrate was evaporated to dryness under reduced pressure and the 24.4 g of semi-crystalline residue were chromtographed over silica gel. Elution with a 95-5 methylene chloride-methanol mixture yielded 6.36 g of 4-O-monoethoxycarbonylpropyl-dienestrol melting towards 86° C.

IR Spectrum (chloroform): Absorption towards 3590 cm$^{-1}$ (OH); towards 1728 cm$^{-1}$ (C=O); towards 1610, 1590, 1573 and 1510 cm$^{-1}$ (aromatic).

STEP B: 4-O-monocarboxypropyl-dienestrol

A mixture of 6.16 g of the product of Step A, 31 ml of 2N sodium hydroxide and 155 ml of methanol was refluxed for one hour and was then cooled to room temperature. The pH of the mixture was adjusted to 5–6 by addition of 7 ml of acetic acid and the mixture was poured into water. The mixture was extracted with ethyl acetate and the organic phase was washed with water, dried, treated with activated carbon and filtered. The filtrate was evaporated to dryness under reduced pressure and the 5.48 g of residue was purified by transformation into the sodium salt and then acidification to the free acid to obtain 5.16 g of 4-O-monocarboxypropyl-dienestrol melting at 158° C.

Analysis: $C_{22}H_{24}O_4$; Calculated: %C: 74.98; %H: 6.86; Found: %C: 74.7; %H: 7.0.

STEP C: Mixed anhydride of isobutyl formate and 4-O-monocarboxypropyl-dienestrol 2.5 mg of the product of Step B, 50 μl of dioxane, 10 μl of a 5:1 dioxane-tri-n-butylamine solution and 10 μl of a 10-1 dioxane-isobutyl chloroformate solution were successively mixed and the resulting solution was stirred under an inert atmosphere for 30 minutes. 3.4 ml of dioxane were added to the mixture to obtain a solution which was used as is for the next step.

STEP D: 4-O-monocarboxypropyl-dienestrol coupled with ($^{125}$I) histamine 1 mCi of sodium iodide $^{125}$I (specific activity of 2000 Ci/mmol) in 5 μl of distilled water was added to 10 μl of a solution of 10$^{-4}$M of histamine in a buffered solution of 0.5M of sodium phosphate with a pH of 8 followed by addition of a mixture of 50 μg of chloramine T and 10 μl of distilled water. The mixture was stirred for 75 seconds and a solution of 300 μg of sodium bisulfite in 10 μl of distilled water were added thereto to obtain an aqueous solution of iodated $^{125}$I histamine with an Rf=0.1 (chromatography over silica gel eluted with a 92-2 methanol-triethylamine mixture).

50 μl of the solution of Step C were added to the solution and the mixture was stirred and stood in the dark at about 4° C. for 2 hours. The mixture was diluted with 0.3 ml of an aqueous 10$^{-1}$M sodium bicarbonate solution and was extracted with 1.5 ml of methylene chloride. The organic phase was evaporated to dryness under an inert atmosphere and the residue was taken up in 100 μl of methylene chloride. The solution was chromatographed over silica gel and eluted with a 97-3 chloroform-methanol mixture to yield 4-O-monocarboxypropyldienestrol coupled with ($^{125}$I) histamine with a total activity of 100 μCi.

EXAMPLE 2

4-O-monocarboxypropyl-hexestrol coupled with ($^{125}$I) histamine

Using the procedure of Step A of Example 1, 20 g of hexestrol were reacted to obtain 6.7 g of 4-O-monoethoxycarbonylpropyl-hexestrol melting towards 110° C.

IR Spectrum (chloroform): Absorption towards 3590 cm$^{-1}$ (OH); towards 1725 cm$^{-1}$ (C=O); at 1610, 1594, 1580 and 1508 cm$^{-1}$ (aromatic).

Using the procedure of Step B of Example 1, the said product was reacted to obtain 4.5 g of 4-O-monocarboxypropylhexestrol melting towards 183° C.

Analysis: $C_{22}H_{28}O_4$; Calculated: %C: 74.13; %H: 7.92; Found: %C: 74.4; %H: 8.1.

Using the procedure of Step C of Example 1, the latter product was reacted to obtain a solution of the mixed anhydride of isobutyl formate and 4-O-monocarboxypropyl-hexestrol.

Using the procedure of Step D of Example 1, the said mixed anhydride was reacted to obtain a 4-O-monocarboxypropyl-hexestrol coupled with ($^{125}$I) histamine with a total activity of 100 μCi.

EXAMPLE 3

Antigen of 4-O-monocarboxypropyl-dienestrol conjugated with bovine seric albumin (BSA)

STEP A: Mixed anhydride of 4-O-monocarboxypropyl-dienestrol and isobutyl formate 0.46 ml of tri-n-butylamine were added to a solution of 352 mg of 4-O-monocarboxypropyl-dienestrol in 10 ml of dioxane and the mixture was stirred under an inert atmosphere. The mixture was cooled to 12° C. and 0.26 ml of isobutyl chloroformate were added thereto. The mixture was stirred at 12° C. for 30 minutes to obtain a solution which was used as is in the next step.

STEP B: Antigen of 4-O-monocarboxypropyl-dienestrol conjugated with bovine seric albumin 1.54 g of bovine seric albumin were added with stirring at 0° C. to a mixture of 44 ml of iced water and 4 ml of dioxane and the resulting solution was subjected to dialysis for 72 hours at a temperature of 1° to 5° C. with a countercurrent of 30 ml of water. The dialysate with a pH of 9 was extracted with iced chloroform and the organic phase was washed with water. The combined aqueous phases congealed and were lyophilized for 20 hours under a reduced pressure of 0.01 mm Hg to obtain 1.4 g of bovine seric albumin.

The said 1.4 g were dissolved in 40 ml of iced dioxane and 1.35 ml of N sodium hydroxide solution were added thereto followed by the mixed anhydride solution of Step A. The pH of the mixture was adjusted to 8.9 by addition of 0.1N hydrochloric acid and the mixture was stirred at 0° C. for 4 hours. The mixture was subjected to dialysis for 18 hours at 1° to 5° C. against water and after the passage of 30 liters of water, the dialysate was acidified to a pH of 4.1 by addition of N and 0.1N hydrochloric acid. The aqueous phase congealed overnight at −18° C. and was then slowly thawed at a temperature less than 5° C. A precipitate formed and the surnagent was removed by filtration. The precipitate was taken up in 100 ml of a 1% sodium bicarbonate solution and the resulting solution was subjected to dialysis for 72 hours under the above conditions. The dialysate was extracted with iced chloroform and the organic phase was washed with water. The combined aqueous phases congealed and were lyophilized for 20 hours under a reduced pressure of 0.01 mg Hg to obtain 1.4 g of the antigen of 4-O-monocarboxypropyl-dienestrol conjugated with bovine seric albumin containing 37 to 38 dienestrol groups per mole.

EXAMPLE 4

Antigen of 4-O-monocarboxypropyl-hexestrol conjugated with bovine seric albumin

Using the procedure of Example 3, 356 mg of 4-O-monocarboxypropyl-hexestrol and 1.54 g of bovine seric albumin were reacted to obtain 1.3 g of the antigen of 4-O-monocarboxypropyl-hexestrol conjugated with bovine seric albumin containing 31 to 32 hexestrol groups per mole.

EXAMPLE 5

Antigen of 4-O-monocarboxypropyl-hexestrol conjugated with human seric albumin

Using the procedure of Example 3, 356 mg of 4-O-monocarboxypropyl-hexestrol and 1.54 g of human seric albumin were reacted to obtain 1.17 g of the antigen of 4-O-monocarboxypropyl-hexestrol conjugated with human seric albumin containing 21 groups of hexestrol per mole.

Various modifications of the products and processes of the invention may be made without departing from the spirit or scope thereof and it is to be understood that the invention is intended to be limited only as defined in the appended claims.

What we claim is:

1. A radioactive stilbene derivative marked with iodine 125 or 131 of the formula

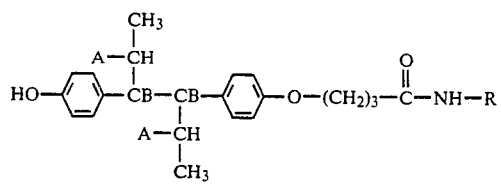

wherein each A and B are both hydrogen or together form a double bond and R is the remainder of amino acid of the formula R—NH$_2$ or a decarboxylated derivative thereof or a lower alkyl ester thereof possessing an iodine acceptor group and marked with iodine 125 or 131.

2. A compound of claim 1 wherein R is selected from the group consisting of histidine, tyrosine, histamine, tyramine and methyl tyrosynate marked with $^{125}$I or $^{131}$I.

3. A compound of claim 1 which is 4-O-monocarboxypropyl-dienestrol coupled with ($^{125}$I) histamine with $^{125}$I in the 2 or 5-position.

4. A compound of claim 1 which is 4-O-monocarboxypropyl-hexestrol coupled with $^{125}$I histamine with $^{125}$I in the 2- or 5-position.

5. In a method for radioimmunological assay dosage of the amount of dienestrol or hexestrol and diethylstilbestrol in warm-blooded animal biological liquids and tissues or feed the improvement comprising using a compound of claim 1 as the radioimmuniological agent.

* * * * *